US00PP14819P3

(12) United States Plant Patent
Macaulay

(10) Patent No.: US PP14,819 P3
(45) Date of Patent: May 25, 2004

(54) IMPATIENS PLANT NAMED 'SNOW 'N ICE'

(50) Latin Name: *Impatiens sultanii*
Varietal Denomination: Snow 'n Ice

(75) Inventor: Alastair Macaulay, Downley High Wycombe (GB)

(73) Assignee: D. S. Cole Growers, Inc., Loudon, NH (US)

( * ) Notice: Subject to any disclaimer, the term of this patent is extended or adjusted under 35 U.S.C. 154(b) by 0 days.

(21) Appl. No.: 10/194,327

(22) Filed: Jul. 15, 2002

(65) Prior Publication Data

US 2004/0010830 P1 Jan. 15, 2004

(51) Int. Cl.[7] ..... A01H 5/00

(52) U.S. Cl. ..... Plt./317

(58) Field of Search ..... Plt./317

*Primary Examiner*—Bruce R. Campell
*Assistant Examiner*—June Hwu
(74) *Attorney, Agent, or Firm*—Foley & Lardner

(57) ABSTRACT

A new and distinct Impatiens plant named 'Snow 'n Ice' characterized by having the distinct color pattern on its leaves which is characteristic of the varieties that make up the Summer Ice® Series of Double flowering Impatiens; and unique white double flower characteristic in combination with the distinct color pattern on its leaves.

2 Drawing Sheets

Latin name of the genus and species of the plant claimed: Genus: Impatiens. Species: *sultanii.*
Variety denomination: 'Snow 'n Ice'.

BACKGROUND OF THE INVENTION

The present invention relates to a new and distinct cultivar of Impatiens plant, botanically known as *Impatiens sultanii,* hereinafter referred to by the cultivar name 'Snow 'n Ice'.

The new cultivar originated from a sport discovered in a cultivated garden in Buckinghamshire, UK. The parent is a white double flowering *Impatiens sultanii.* 'Snow 'n Ice' was discovered and selected by the inventor, Alastair Macaulay, as a flowering plant within the progeny in the controlled environment of his garden.

Asexual reproduction of the new cultivar by tip cuttings was first performed late 2000 in Buckinghamshire, United Kingdom and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be basic characteristics of 'Snow 'n Ice' which in combination distinguish this Impatiens as a new and distinct cultivar:

1. Impatiens 'Snow 'n Ice' has the distinct color pattern on its leaves which is characteristic of the varieties that make up the Summer Ice® Series of Double flowering Impatiens; and
2. unique white double flower characteristic in combination with the distinct color pattern on its leaves.

'Snow 'n Ice' has not been observed under all possible environmental conditions. The phenotype of the new cultivar may vary significantly with variations in environment such as temperature, light intensity, and daylength without any change in the genotype of the plant. The following observations, measurements and values describe the new cultivar as grown in Loudon, N.H. under conditions which closely approximate those generally used in commercial practice.

Of the many commercial cultivars known to the present inventor, the most similar in comparison to 'Snow 'n Ice' is cultivar 'Pink Ice'. The plant growth habit, foliage appearance and leaf variegation is similar. The flower color is distinctly different. Mature 'Pink Ice' flowers are pink, RHS 75B with darker 74 B throat and main color fading to RHS 75C; immature flowers are between RHS 74 D and RHS 75B. 'Snow 'n Ice' flowers are white, RHS 155 C.

In comparison to its parent, 'Snow 'n Ice' differs in that it has distinctly variegated foliage. The leaves of the parent plant have the shades of green common to *Impatiens sultanii.* The upper surface of the mature leaves of 'Snow 'n Ice' are green with a silver sheen, RHS 188A, with a green center RHS 189A, and a white fringe, RHS 155B. 'Snow 'n Ice' also differs in growth habit from its parent plant, taking approximately 1 to 2 weeks longer to bloom, and having a slower growth, rate 2 to 3 weeks behind the parent plant due to the reduced amount of chlorophyll.

BRIEF DESCRIPTION OF THE DRAWING

The accompanying photographic drawings illustrate the overall appearance of the new Impatiens showing the colors as true as is reasonably possible with colored reproductions of this type.

1. The first drawing shows a whole plant view of a flowering potted 'Snow 'n Ice';
2. The second drawing shows a close-up view of the foliage and inflorescences of 'Snow 'n Ice'.

DETAILED BOTANICAL DESCRIPTION

The following observations, measurements and values describe the new cultivar as grown in Loudon, N.H. under conditions which closely approximate those generally used in commercial practice. The cultivar was grown under commercial greenhouse conditions at a temperature of 60–65 degree F. nights and 70–75 F. days. Color references are made to The Royal Horticultural Society Colour Chart (R.H.S.), except where general colors of ordinary significance are used. Color values were taken under daylight conditions at approximately 9 to 11 AM in Loudon, N.H. The age of the plant described is 9 months.

Propagation: stem cutting.

Plant:

*General appearance and form.*—Height: 7 inches in a 6 inch diameter pot; 9 inches in a 16 inch diameter pot. Plant spread: 6–7 inches, depending upon age and container size. Lateral branches: Average 4 inches in length; average ⅛ inches in diameter. Internode length ½ inch to 1 inch. Color including anthocyanin color RHS 144B. Flowering Season: Year round as grown in a greenhouse, best in spring. Winter hardiness: To USDA zone 10. Lastingness of the Individual Bloom: Approximately 1 week. Rooting habit: Fibrous root system. Time to initiate roots: 7 days at 21° C. year round. Time to produce a rooted cutting or liner: 3 weeks. Growth and branching habit: Mounded form with good branching. Slower growth than green leaved varieties. Crop time: 6 weeks for a 10 cm pot; 8–10 weeks for larger pots. Fragrance: None.

Foliage:

*Overall shape of leaf.*—Ovate.

*Apex.*—Acuminate.

*Base.*—Cuneate.

*Length.*—¾ inch to 1 inch in a 6 inch pot; 1 inch to 1¼ inch in a 16 inch pot.

*Width.*—¾ inch maximum in a 6 inch pot; 1 inch maximum in a 16 inch pot.

*Margin.*—Slightly serrate.

*Texture.*—Smooth with some wrinkling, slightly waxy.

*General color.*—Foliage color is comprised of three colors or shades: green, green with a silver sheen, and a white margin which varies in width, all in varying percentages.

*Color of upper surface.*—Mature leaf: Green with a silver sheen RHS 188A, green center RHS 189A. White fringe (up to 25% of total leaf area) RHS 155B. Immature leaf: Green with a silver sheen RHS 188A, green center RHS 147A. White fringe (up to 25% of total leaf area) RHS 158B.

*Color of lower surface.*—Mature leaf: Green center RHS 148D. White fringe RHS 155B. Immature leaf: Green center RHS 191D. White fringe RHS 158B.

*Venation color.*—Upper surface: Same as leaf color. Lower surface: RHS 146A.

*Petiole.*—Length: Highly variable dependant upon maturity, ranging from ⅛ inch to 1 inch. Diameter: 1/32 inch to 1/16 inch. Color: Ranging from RHS 146A young to RSH 148C at maturity. Surface texture: Smooth, slightly waxy.

Inflorescence:

*Flower type and habit.*—Flowers start as a bud the shape of a round ball and the size of a pea, and open similar to a rose in fullness. The flowers open slightly above or even with the foliage. The flower is fully double.

*Flower size.*—1.25 to 2.0 inches.

*Overall shape.*—Dome shape.

*Average number of flowers per lateral branch.*—In bloom, 2; inclusive of buds, 4 to 5.

*Petals.*—Petal Number: Average 27–32. Petal Shape: Round to slightly oblong with indentation in tip. Texture: Smooth. Petal size: Length ⅜ inch to ⅝ inch; width ½ inch to ¾ inch. Petal Color: RHS 155C (both surfaces).

*Sepals.*—Sepal Number: 2 (1 with a spur). Sepal Shape: Rounded to ovate, acuminate to rounded apex; margin entire. Texture: Smooth. Sepal Size: Length ¼ inch to ⅜ inch; width ¼ inch to ½ inch.

*Spur.*—½ to ¾ in length; greenish-white in color RHS 157C.

*Stem.*—Average length: 2 inches in a 6 inch pot (pinched plants). Average diameter: ¼ inch (pinched). Color: RHS 144A. Surface Texture: Smooth, slightly waxy. Internode length: Average ¼ inch, highly dependent on available light.

*Bud.*—Rate of opening: 5 days from a mature bud. Color of mature buds: Basically white RHS 155B (95% of bud), with a slight touch of green RHS 145A (5% of bud). White color comes out as soon as bud cracks open. Color of immature buds: White RHS 155B (60% of bud), and green RHS 145A (40% of bud). Shape: Ovular with a flat base.

*Length.*—⅜ to ½ inch (mature bud).

*Diameter.*—¼ inch to ⅜ inch (mature bud).

*Peduncles* (*pedicels*).—½ to 1 inch in length at a 45° angle. Strength is weak.

Reproductive organs:

*Stamen.*—Present but sterile; multiple in number; color RHS 151B.

*Seeds.*—None.

*Fruit.*—None.

*Anthers.*—Indistinguishable from stamen; color RHS 151B.

*Pollen.*—Indistinguishable from anthers/stamen color RHS 151B.

*Stigma.*—Present, sterile; yellow in color.

*Ovary.*—Not distinctive.

Disease resistance: Some resistance to Botrytis, root Fungi seldom problematic.

I claim:

1. A new and distinct Impatiens plant named 'Snow n' Ice', substantially as illustrated and described herein.

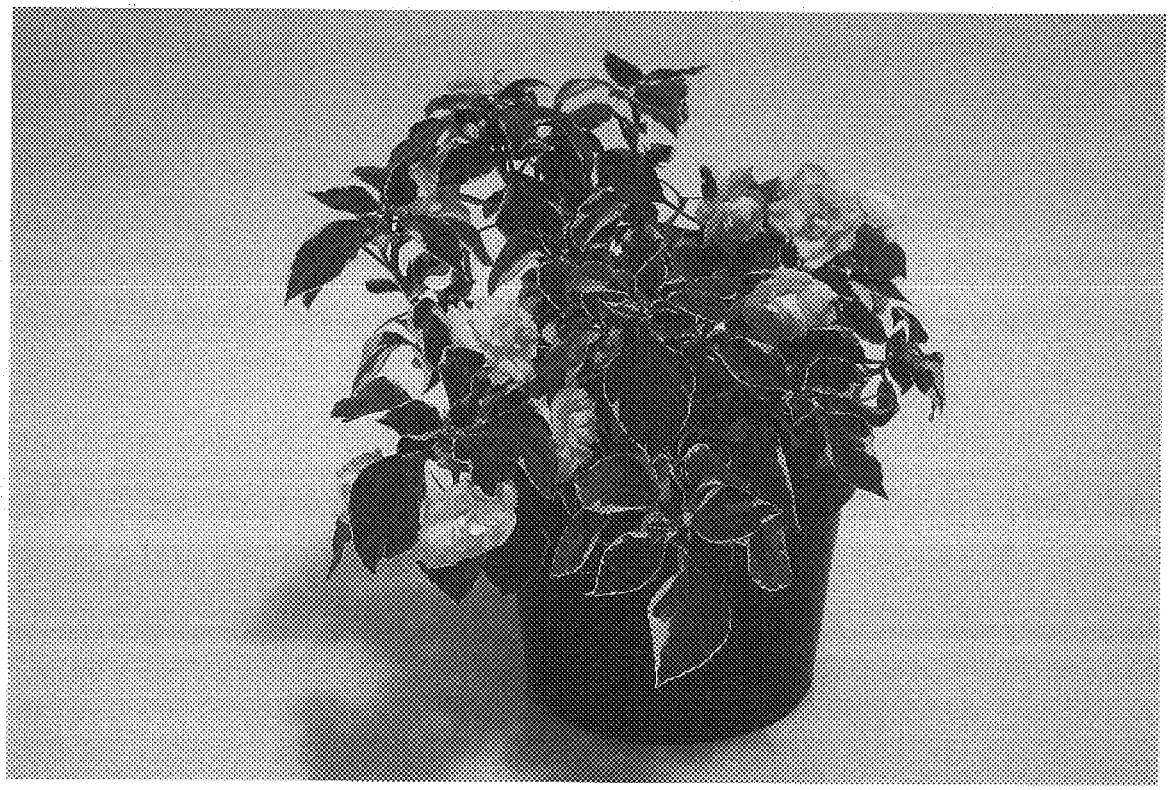

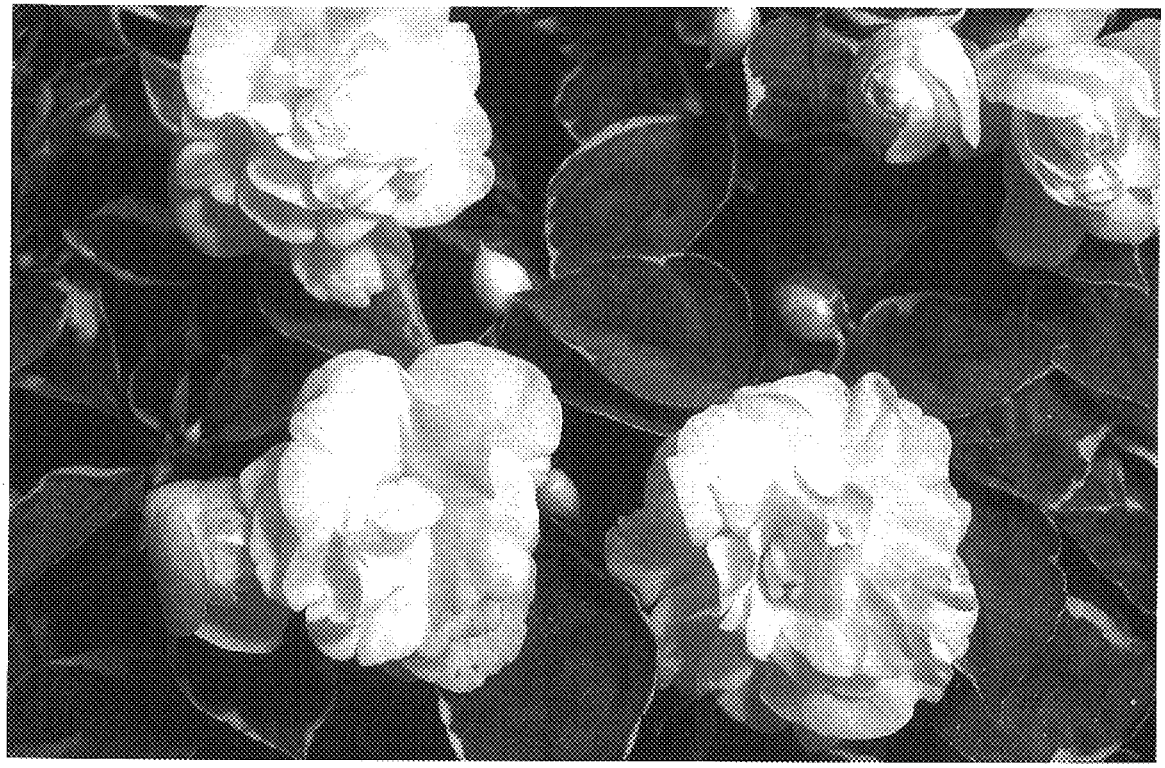

* * * * *